(12) United States Patent
Kim et al.

(10) Patent No.: US 12,176,721 B2
(45) Date of Patent: Dec. 24, 2024

(54) APPARATUS FOR TRANSMITTING POWER WIRELESSLY USING CAPACITIVE COUPLING

(71) Applicant: Industry-Academic Cooperation Foundation, Chosun University, Gwangju (KR)

(72) Inventors: Youn Tae Kim, Daejeon (KR); Da Eun Kim, Gwangju (KR); Jae Hyo Jung, Gwangju (KR); Si Ho Shin, Gwangju (KR)

(73) Assignee: Industry-Academic Cooperation Foundation, Chosun University, Gwangju (KR)

( * ) Notice: Subject to any disclaimer, the term of this patent is extended or adjusted under 35 U.S.C. 154(b) by 572 days.

(21) Appl. No.: 17/534,117

(22) Filed: Nov. 23, 2021

(65) Prior Publication Data
US 2022/0376550 A1    Nov. 24, 2022

(30) Foreign Application Priority Data
May 18, 2021  (KR) .................. 10-2021-0063759

(51) Int. Cl.
| | | |
|---|---|---|
| H01M 10/46 | (2006.01) | |
| A61N 1/378 | (2006.01) | |
| H02J 50/00 | (2016.01) | |
| H02J 50/05 | (2016.01) | |
| H02J 50/40 | (2016.01) | |

(52) U.S. Cl.
CPC .......... *H02J 50/05* (2016.02); *A61N 1/3787* (2013.01); *H02J 50/005* (2020.01); *H02J 50/402* (2020.01)

(58) Field of Classification Search
CPC ........ H02J 50/05; H02J 50/005; H02J 50/402; H02J 7/342; A61N 1/3787
USPC ................ 320/101, 107, 108, 114, 115, 116
See application file for complete search history.

(56) References Cited

U.S. PATENT DOCUMENTS

| | | | |
|---|---|---|---|
| 2016/0079765 A1 | 3/2016 | Jeong et al. | |
| 2021/0211815 A1 | 7/2021 | Fritzsche et al. | |
| 2023/0268773 A1* | 8/2023 | Hata ...................... | H02J 50/80 307/104 |

FOREIGN PATENT DOCUMENTS

| | | |
|---|---|---|
| JP | 2010148287 A | 7/2010 |
| KR | 10-2016-0030803 A | 3/2016 |
| KR | 20210013603 A | 2/2021 |

OTHER PUBLICATIONS

Machine translate JP2010148287 (Jul. 1, 2010) (Year: 2010).*

(Continued)

*Primary Examiner* — Edward Tso
(74) *Attorney, Agent, or Firm* — Renner, Otto, Boisselle & Sklar, LLP.

(57) ABSTRACT

An apparatus for transmitting power wirelessly using capacitive coupling, provided in a wearable device, includes: a transmission electrode including a plurality of unit electrode pairs, each unit electrode pair being formed by a transmission signal electrode and a transmission ground electrode; and a control module configured to select a unit electrode pair, forming capacitive coupling with the reception electrode, among the plurality of unit electrode pairs provided in the reception electrode, to wirelessly transmit power to a reception electrode included in an implantable device.

11 Claims, 5 Drawing Sheets

(56) References Cited

OTHER PUBLICATIONS

Machine translate KR20210013603 (Feb. 4, 2021) (Year: 2021).*
Korean Office Action issued by the Korean Intellectual Property Office corresponding to counterpart Korean patent application No. 20210063759, dated Jan. 30, 2023.

* cited by examiner

APPARATUS FOR TRANSMITTING POWER WIRELESSLY USING CAPACITIVE COUPLING

CROSS-REFERENCE TO RELATED APPLICATION(S)

The present application claims the benefit of priority to Korean Patent Application No. 10-2021-0063759, filed on May 18, 2021 in the Korean Intellectual Property Office, the entire disclosure of which is incorporated herein by reference.

BACKGROUND

1. Field

The present disclosure relates to an apparatus for transmitting power wirelessly using capacitive coupling, provided in a wearable device.

2. Description of Related Art

Implantable electronic medical devices are medical devices implanted into portions corresponding to body organs such as heart, kidneys, ears, and the like, to replace functions of defective body organs. As an example, such implantable electronic medical devices may include various products such as an implantable cardiac pacemaker, an implantable medical infusion pump, an implantable cochlear system, and the like. Such products may be combined with various technologies including microprocessors, wireless communications circuits, and the like, but there is a need for further miniaturization. In the future, implantable electronic medical devices are expected to expand to body insertable devices such as real-time blood glucose analyzers, disease diagnosis sensors, blood analysis sensors, and the like.

Batteries are required to operate such devices. To this end, wireless charging technologies using coils have been applied.

In the case of wireless charging using coils, a transmission coil disposed outside a human body and a reception coil disposed inside the human body should be aligned with each other to achieve efficient charging. A magnet may be used to align the transmission coil and the reception coil with each other but, unlike the case in which a magnet is applied to general devices, in the case in which a magnet is used in a human body, strong magnetic force may be required for accurate alignment. However, a reception coil disposed below the skin may cause a large amount of force to be applied to the skin at the time of separation therebetween, so that it may be difficult to apply a magnet to a human body.

In addition, when power is supplied to an implantable device disposed inside the human body, transmitting power through a large amount of current or a high voltage in a short time may generate heat, which may cause a user to feel uncomfortable and may result in side effects.

SUMMARY

An aspect of the present disclosure is to provide an apparatus for transmitting power wirelessly, which may significantly improve efficiency of wireless power transmission.

Another aspect of the present disclosure is to provide an apparatus for transmitting power wirelessly, which may effectively deal with a wireless power transmission failure caused by a rotational error between a reception electrode of an implantable device, disposed around an ear, and a wearable device, making contact with a human body, in the form of a circle such as a shape of a headphone.

Another aspect of the present disclosure is to provide an apparatus for transmitting power wirelessly, which may achieve continuous wearing and power supply without a limitation in user activity for charging.

According to an aspect of the present disclosure, an apparatus for transmitting power wirelessly using capacitive coupling, provided in a wearable device, includes: a transmission electrode including a plurality of unit electrode pairs, each unit electrode pair being formed by a transmission signal electrode and a transmission ground electrode; and a control module configured to select a unit electrode pair, forming capacitive coupling with the reception electrode, among the plurality of unit electrode pairs provided in the reception electrode, to wirelessly transmit power to a reception electrode included in an implantable device.

The control module may apply an AC voltage to the plurality of unit electrode pairs in units of unit electrode pairs and, when current flowing through the reception electrode and a unit electrode pair by the applied AC power is sensed, may determine that capacitive coupling is formed between a unit electrode pair applied with an AC voltage and the reception electrode.

The apparatus may further include: a switch module including a plurality of switches configured to open and close a connection between the control module and a transmission signal electrode and a reception signal electrode of the reception electrode.

The control module may control the switch module such that AC power is sequentially applied in units of the unit electrode pairs.

The transmission signal electrode and the transmission ground electrode may be provided such that adjacent electrodes are disposed to be spaced apart from each other by a predetermined distance on the same plane.

The transmission signal electrode and the transmission ground electrode may be provided such that adjacent electrodes are alternately disposed on two different planes and there is no gap between adjacent electrodes, when viewed from above.

Each of the transmission signal electrode and the transmission ground electrode may have a fan shape.

The transmission signal electrode and the transmission ground electrodes may be provided such that electrodes disposed in a center thereof are formed to be wide, and electrodes disposed on an external surface thereof are formed to be narrow.

The wearable device may be glasses, and the transmission electrode may be provided on either one or both temples of the glasses.

The temple of the glasses may be attachable to or detachable from a body of the glasses including a lens.

The wearable device may be a headphone, and the transmission electrode may be provided in a contact portion in contact with skin around an ear.

BRIEF DESCRIPTION OF DRAWINGS

The above and other aspects, features, and advantages of the present disclosure will be more clearly understood from the following detailed description, taken in conjunction with the accompanying drawings.

DETAILED DESCRIPTION

Hereinafter, example embodiments of the present disclosure will be described in detail with reference to the accompanying drawings. The present disclosure may, however, be embodied in many different forms, and should not be construed as being limited to the embodiments set forth herein. Rather, these embodiments are provided so that this disclosure will be thorough and complete, and will fully convey the scope of the invention to those skilled in the art. In the drawings, the shapes and dimensions may be exaggerated for clarity, and the same reference numerals will be used throughout to designate the same or like components.

Figure 1:
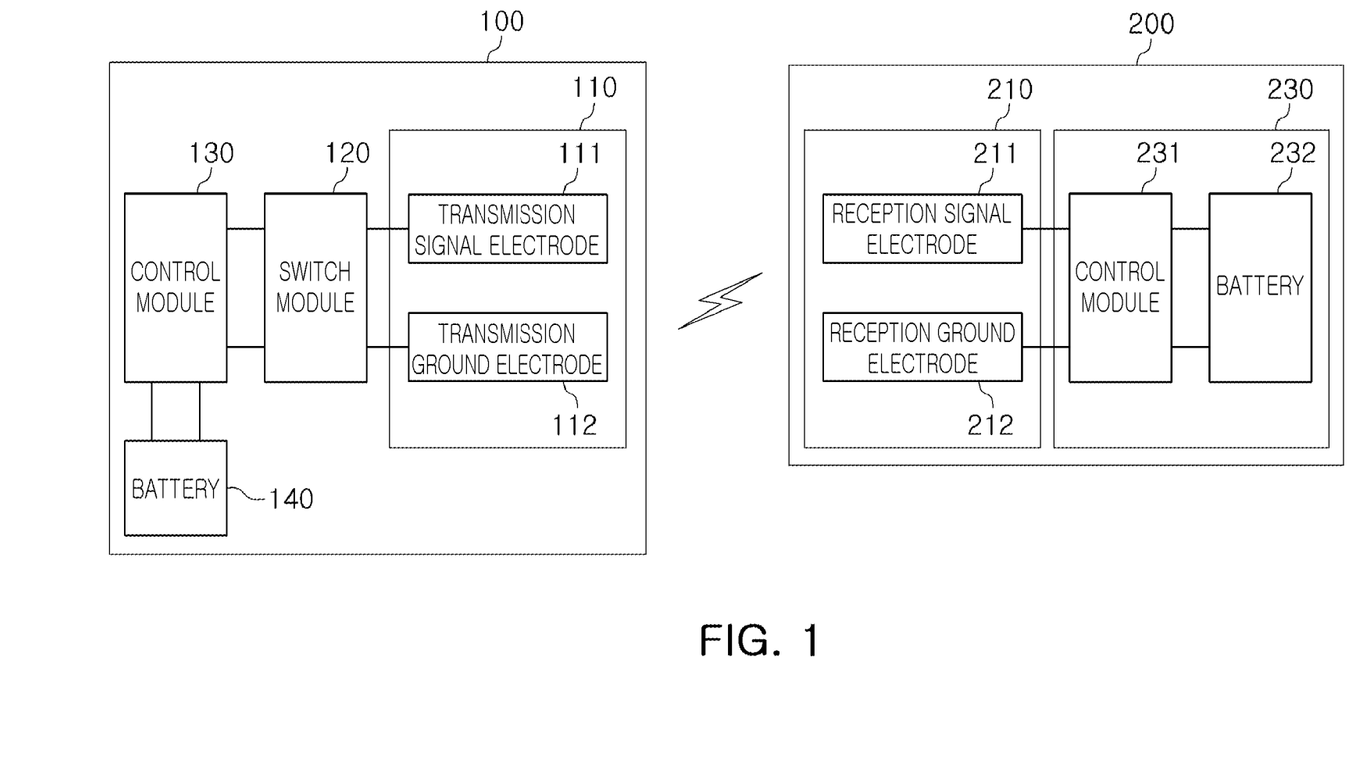
FIG. 1 is a block diagram illustrating internal structures of an apparatus for transmitting power wirelessly and an apparatus for receiving power wirelessly according to an example embodiment of the present disclosure.
Figure 2A:
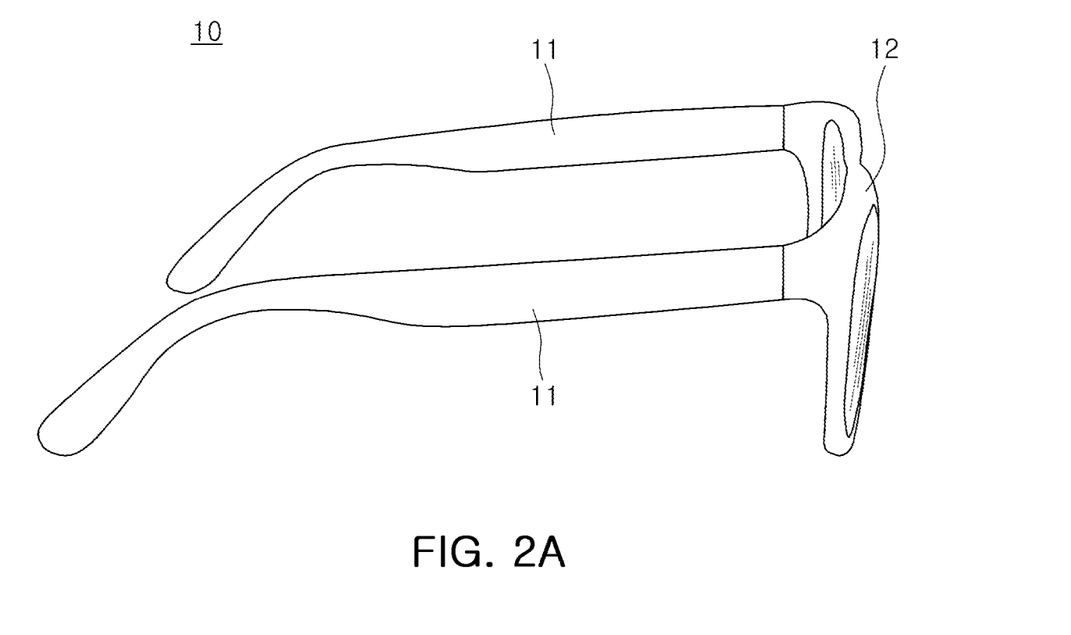
FIG. 2A is a diagram illustrating a wearable device provided with an apparatus for transmitting power wirelessly according to an example embodiment of the present disclosure.

FIG. 1 is a block diagram illustrating internal structures of an apparatus for transmitting power wirelessly and an apparatus for receiving power wirelessly according to an example embodiment. FIG. 2A is a diagram illustrating a wearable device provided with an apparatus for transmitting power wirelessly according to an example embodiment, and FIG. 2B is a diagram illustrating a transmission electrode provided in a wearable device and a reception electrode provided in an implantable device according to an example embodiment.

Figure 2B:
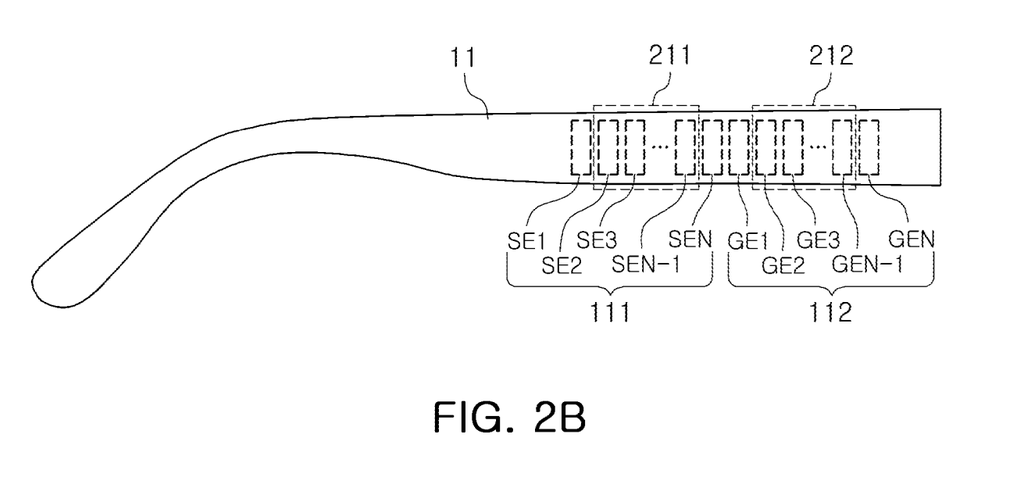
FIG. 2B is a diagram illustrating a transmission electrode provided in a wearable device and a reception electrode provided in an implantable device according to an example embodiment of the present disclosure.

As illustrated in FIGS. 1 to 2B, an apparatus 100 for transmitting power wirelessly according to an example embodiment may be provided in a wearable device, and may include a transmission electrode 110, a switch module 120, a control module 130, and the battery 140. It will be noted that the apparatus 100 for transmitting power wirelessly may further include a communications module communicating with an external device to transmit power or setting information of the wearable device.

When the above-described wearable device is the glasses as illustrated in FIGS. 2A and 2B, the apparatus 100 for transmitting power wirelessly, in particular, the transmission electrode 110 may be provided on either one or both temples 11 of the glasses 10. In addition, the temple 11 of the glasses 10 may be configured to be detachable from the body 12 of the glasses 10 including a lens, which will be described later with reference to FIG. 6.

In addition, when the above-described wearable device is, for example, a headphone, the apparatus 100 for transmitting power wirelessly, in particular, the transmission electrode 110 may be provided in a contact portion in contact with skin around an ear.

The transmission electrode 110 of the apparatus 100 for transmitting power wirelessly may include a plurality of unit electrode pairs in which a transmission signal electrode 111 and a transmission ground electrode 112 form a pair.

For example, as illustrated in FIG. 2B, in the unit electrode pair, the transmission signal electrode 111 and the transmission ground electrode 112 form a pair. For example, SE1-GE1, SE2-GE2, SE3-GE3, SEN-1-GEN-1, and SEN-GEN may each be a unit electrode pair.

The transmission signal electrode 111 may face a reception signal electrode 211 of an implantable device, and the transmission ground electrode 112 may face a reception ground electrode 212 of the implantable device to wirelessly transmit power using a capacitive coupling method.

The transmission electrode 110 of the wearable device and a reception electrode 210 of the implantable device constitute two metal plates. In addition, when a time-varying AC voltage is applied to the transmission electrode 110, displacement current may be generated and a corresponding AC voltage may be generated on the reception electrode 210 to wirelessly transmit power.

The control module 130 of the apparatus 100 for transmitting power wirelessly may select a unit electrode pair, forming a capacitive coupling with the reception electrode 210, among a plurality of unit electrode pairs provided in the transmission electrode 110. Then, power may be wirelessly transmitted to the implantable device through the selected unit electrode pair.

The control module 130 may apply an AC voltage to the plurality of unit electrode pairs in units of unit electrode pairs to select a unit electrode pair. To this end, the control module 130 may include a circuit converting DC power, stored in the battery 140, into AC power.

Then, when current flowing through the reception electrode 210 and the unit electrode pair is sensed by the applied AC power, the control module 130 may confirm that capacitive coupling is formed between the unit electrode pair, to which the AC voltage is applied, and the reception electrode 210. This will be described later in detail with reference to FIG. 3.

In addition, the control module 130 may control the switch module 120 to be described later such that AC power is sequentially applied in units of unit electrode pairs.

The switch module 120 of the apparatus 100 for transmitting power wirelessly may include a plurality of switches opening and closing a connection between the control module 130 and the transmission signal electrode 111 and the transmit ground electrode 112 of the transmission electrode 110.

Similarly, an apparatus 200 for receiving power wirelessly may be provided in the implantable device and may include a reception electrode 210 and a reception circuit 230, and the reception circuit 230 may include a control module 231 and a battery 232. The above-described implantable device may include various devices, insertable into the human body, such as an implantable cardiac pacemaker, an implantable medical infusion pump, an implantable cochlear system, and the like.

The reception electrode 210 of the apparatus 200 for receiving power wirelessly may include a reception signal electrode 211 and a reception ground electrode 212, respectively configured to face the transmission signal electrode 111 and the transmission ground electrode 112 of the wearable device, and may receive power wirelessly through capacitive coupling. Unlike the transmission electrode 210, the reception signal electrode 211 and the reception ground electrode 212 of the reception electrode 210 may include a single electrode.

The control module 231 of the apparatus for receiving power wirelessly may receive power wirelessly through capacitive coupling, and may store the received power in the battery 232.

Figure 3:
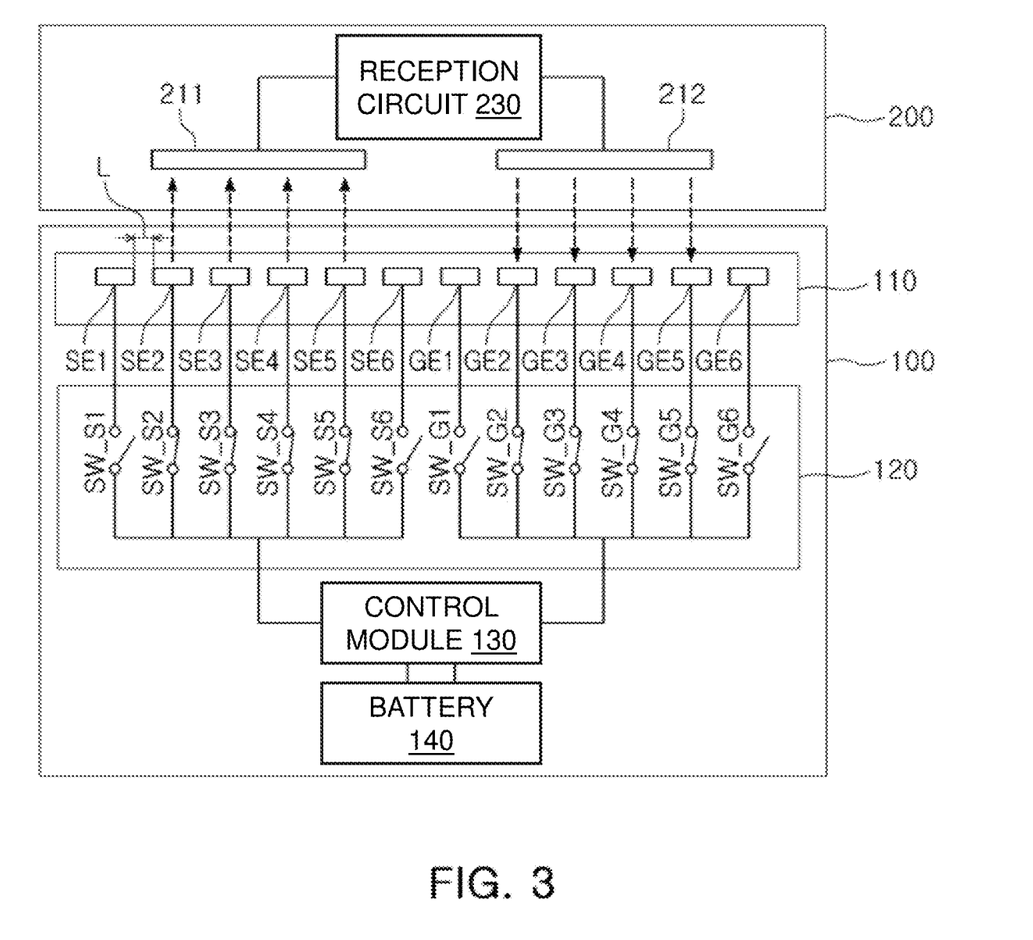
FIG. 3 is a diagram illustrating a process of determining whether capacitive coupling is formed between a reception electrode and a unit electrode pair according to an example embodiment of the present disclosure.

FIG. 3 is a diagram illustrating a process of determining whether capacitive coupling is formed between a reception electrode and a unit electrode pair according to an example embodiment.

Hereinafter, a process of determining whether a capacitive coupling is formed between a receiving electrode and a unit electrode pair according to an example embodiment will be described with additional reference to FIG. 3.

FIG. 3 illustrates a transmission electrode 110 in which electrodes are disposed to be spaced apart from each other by a predetermined distance L on the same plane.

Specifically, as illustrated in FIG. 3, a control module 130 may convert DC power, stored in a battery 140, into AC power and may control a switch module 120 to apply the AC power to a plurality of unit electrode pairs in units of unit electrode pairs.

Specifically, the control module 130 may turns on switches SW_S1 and SW_G1 to apply an AC voltage to a unit electrode pair SE1-GE1, and may then sense current flowing through a transmission electrode 210 and the unit electrode pair SE1-GE1. As illustrated in FIG. 3, the reception electrode 210 and the unit electrode pair SE1-GE1 are offset from each other, so that capacitive coupling may not be formed between the reception electrode 210 and the unit electrode pair SE1-GE1, and thus, no current may be detected. Accordingly, the control module 130 may determine that the reception electrode 210 and the unit electrode pair SE1-GE1 do not form capacitive coupling. Then, the control module 130 may turn off the switches SW_S1 and SW_G1.

Next, the control module 130 may turn on switches SW_S2 and SW_G2 to apply an AC voltage to a unit electrode pair SE2-GE2, and may then sense current flowing through the reception electrode 210 and the unit electrode pair SE2-GE2. As illustrated in FIG. 3, the reception electrode 210 and the unit electrode pair SE2-GE2 face each other, so that capacitive coupling may be formed between the reception electrode 210 and the unit electrode pair SE2-GE2, and thus current may be sensed. The control module 130 may select the unit electrode pair SE2-GE2. Then, the control module 130 may turn off the switches SW_S2 and SW_G2.

Similarly, the control module 130 may sequentially turn on switches SW_S3 and SW_G3 to SW_S6 and SW_G6 to sense current in the same manner. As a result, as illustrated in FIG. 3, the control module 130 may determine that the reception electrode 210 and the unit electrode pair SE2-GE2, the reception electrode 210 and the unit electrode pair SE3-GE3, and the reception electrode 210 and the unit electrode pair SE4-GE4, and the reception electrode 210 and the unit electrode pair SE5-GE5 form capacitive coupling, and may select the unit electrode pair SE2-GE2 and the unit electrode pair SE2-GE2, the unit electrode pair SE4-GE4, and the unit electrode pair SE5-GE5 may be selected as electrodes for wireless power transmission.

Then, the control module 130 may wirelessly transmit power to the implantable device through the selected unit electrode pair.

Figure 4:
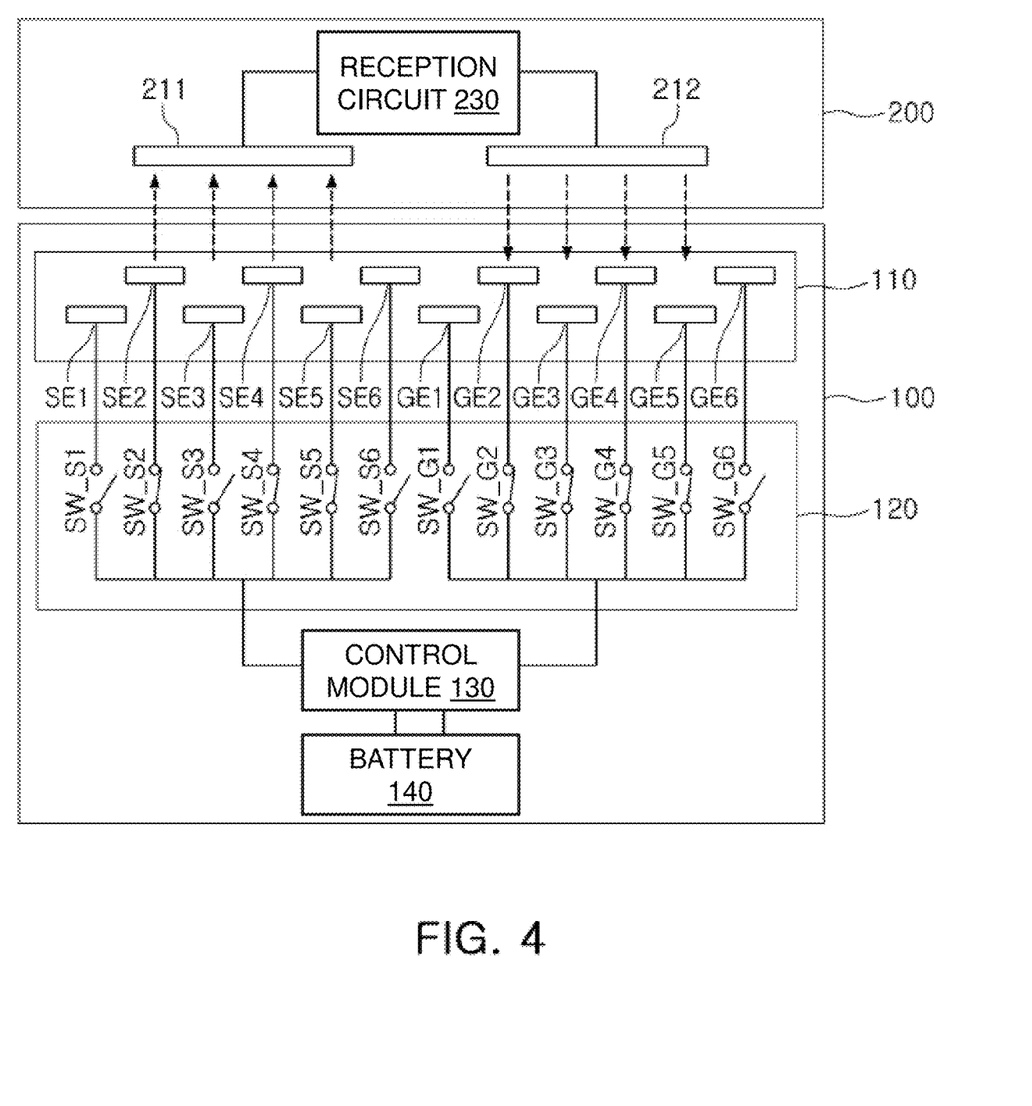
FIG. 4 is a diagram illustrating transmission electrodes alternately disposed on two planes according to an example embodiment of the present disclosure.

FIG. 4 is a diagram illustrating transmission electrodes alternately disposed on two planes according to an example embodiment.

Unlike the embodiment of FIG. 3, in the embodiment of FIG. 4, transmission signal electrodes SE1 to SE6 and transmission ground electrodes GE1 to GE6 may be configured such that adjacent electrodes are alternately disposed on two different planes and there is no gap between the adjacent electrodes, when viewed from above. The transmission signal electrodes SE1 to SE6 and the transmission ground electrodes GE1 to GE6, formed on the different planes, may be manufactured using a conventional semiconductor process or a process of forming a multilayer structure such as a printed circuit board (PCB) or a flexible PCB (FPCB).

According to the above-described embodiment, transmission signal electrodes and transmission ground electrodes may be configured such that adjacent electrodes are alternately disposed and there is no gap between the adjacent electrodes, when viewed from above. Thus, an area of the transmission electrode may be increased to significantly improve efficiency of wireless power transmission.

Figure 5:
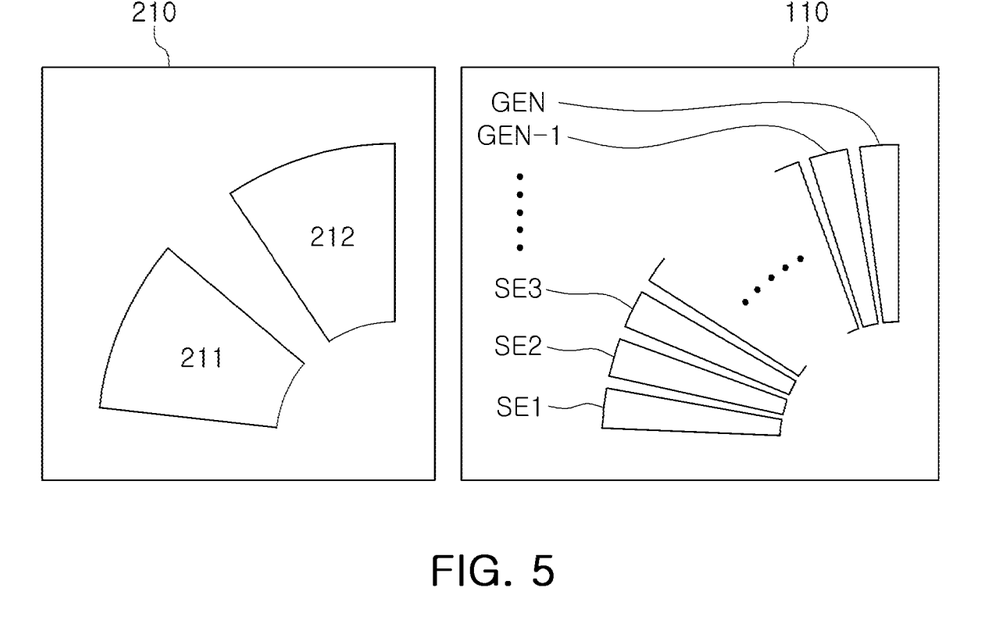
FIG. 5 is a diagram illustrating a fan-shaped transmission electrode according to an example embodiment of the present disclosure.

FIG. 5 is a diagram illustrating a fan-shaped transmission electrode according to an example embodiment of the present disclosure.

As illustrated in FIG. 5, in a reception electrode 210 of an implantable device, a reception signal electrode 211 and a reception ground electrode 212 may each have a fan shape. Accordingly, a transmission signal electrode and a transmission ground electrode of a transmission electrode 110 provided in the wearable device may also each have a fan shape.

According to the above-described embodiment, each of the transmission signal electrode and the transmission ground electrode may be configured to have a fan shape, which may effectively deal with a wireless power transmission failure caused by a rotational error between a reception electrode of an implantable device, disposed around an ear, and a wearable device, making contact with a human body, in the form of a circle such as a shape of a headphone.

In addition, according to an example embodiment, the transmit signal electrode and the transmit ground electrode may be provided such that electrodes disposed in a center thereof are formed to be wide, and electrodes disposed on an external surface thereof are formed to be narrow.

Figure 6:
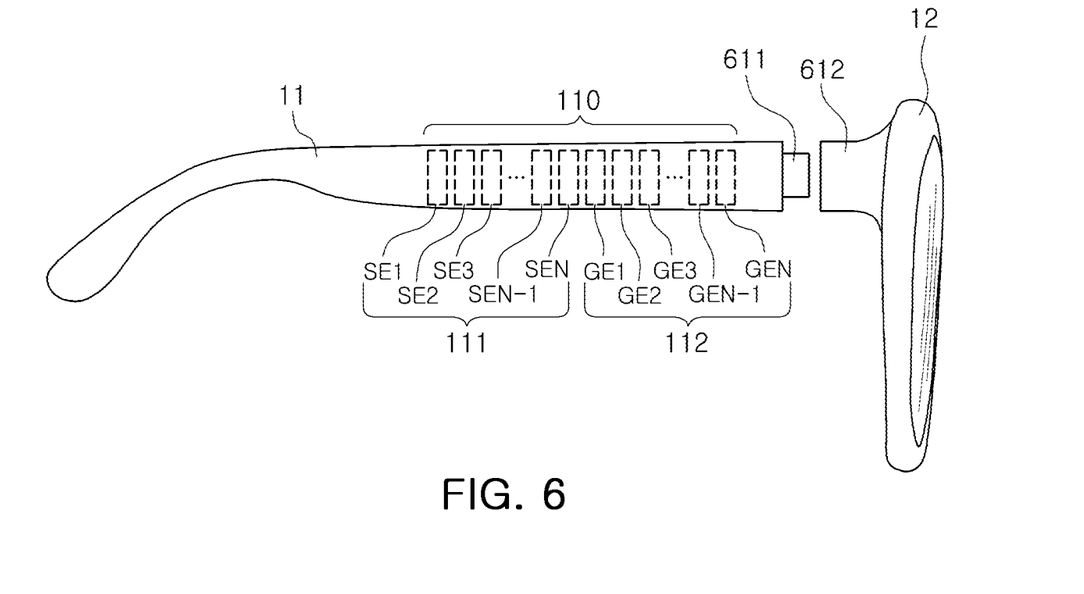
FIG. 6 is a diagram illustrating a body of glasses, including a lens, and a temple of the glasses, provided with a detachable apparatus for transmitting power wirelessly, according to an example embodiment of the present disclosure.

FIG. 6 is a diagram illustrating a body of glasses, including a lens, and a temple of the glasses, provided with a detachable apparatus for transmitting power wirelessly, according to an example embodiment of the present disclosure.

As illustrated in FIG. 6, a temple 11 of glasses may be configured to be detachable from a body 12 of the glasses including a lens. To this end, the temple 11 of the glasses may include a first coupling portion 611, and the body 12 of the glasses may include a second coupling portion 612, and the temple 11 of the glasses may be easily attached to and detached from the body 12 of the glasses through the first coupling portion 611 and the second coupling portion 612.

According to an example embodiment, the temples of the glasses provided with an apparatus for transmitting power wirelessly may be detachable from the body of the glasses including the lenses, which may achieve continuous wearing and power supply without a limitation in user activity for charging.

As described above, according to example embodiments, a unit electrode pair formed by a transmission signal electrode and a transmission ground electrode may be provided in plural. Among the plurality of unit electrode pairs, a unit electrode pair forming capacitive coupling with a reception electrode of an implantable device may be selected to significantly improve efficiency of wireless power transmission.

In addition, according to example embodiments, transmission signal electrodes and transmission ground electrodes may be configured such that adjacent electrodes are alternately disposed on two different planes and there is no gap between the adjacent electrodes, when viewed from above. Thus, an area of the transmission electrode may be increased to significantly improve efficiency of wireless power transmission.

In addition, according to example embodiments, each of the transmission signal electrode and the transmission ground electrode may be configured to have a fan shape, which may effectively deal with a wireless power transmission failure caused by a rotational error between a reception electrode of an implantable device, disposed around an ear, and a wearable device, making contact with a human body, in the form of a circle such as a shape of a headphone.

In addition, according to example embodiments, temples of glasses provided with an apparatus for transmitting power wirelessly may be detachable from a body of the glasses including lenses, which may achieve continuous wearing and power supply without a limitation in user activity for charging.

While exemplary embodiments have been shown and described above, it will be apparent to those skilled in the art that modifications and variations could be made without departing from the scope of the present disclosure as defined by the appended claims.

What is claimed is:

1. An apparatus for transmitting power wirelessly using capacitive coupling, provided in a wearable device, the apparatus comprising:
    a transmission electrode including a plurality of unit electrode pairs, each unit electrode pair being formed by a transmission signal electrode and a transmission ground electrode; and
    a control module configured to select a unit electrode pair, forming capacitive coupling with a reception electrode, among the plurality of unit electrode pairs provided in the transmission electrode, to wirelessly transmit power to the reception electrode included in an implantable device.

2. The apparatus of claim 1, wherein:
the control module applies an AC voltage to each unit electrode pair of the plurality of unit electrode pairs and, when current flowing through the reception electrode and a unit electrode pair is sensed, determines that capacitive coupling is formed between a unit electrode pair to which the AC voltage is applied and the reception electrode.

3. The apparatus of claim 2, further comprising:
a switch module including a plurality of switches configured to open and close a connection between the control module and a transmission signal electrode and a reception signal electrode of the reception electrode.

4. The apparatus of claim 3, wherein:
the control module controls the switch module such that AC power is sequentially applied to each unit electrode pairs.

5. The apparatus of claim 1, wherein:
the transmission signal electrode and the transmission ground electrode are provided such that adjacent electrodes are disposed to be spaced apart from each other by a predetermined distance on a same plane.

6. The apparatus of claim 1, wherein:
the transmission signal electrode and the transmission ground electrode are provided such that adjacent electrodes are alternately disposed on two different planes and there is no gap between adjacent electrodes.

7. The apparatus of claim 1, wherein:
the transmission signal electrode and the transmission ground electrode have a fan shape.

8. The apparatus of claim 1, wherein:
the transmission signal electrode and the transmission ground electrodes are provided such that electrodes disposed in a center thereof are formed to be wide, and electrodes disposed on an external surface thereof are formed to be narrow.

9. The apparatus of claim 1, wherein:
the wearable device is glasses; and
the transmission electrode is provided on either one or both temples of the glasses.

10. The apparatus of claim 9, wherein:
the temple of the glasses is attachable to or detachable from a body of the glasses including a lens.

11. The apparatus of claim 7, wherein:
the wearable device is a headphone; and
the transmission electrode is provided in a contact portion in contact with skin around an ear of a user.

* * * * *